United States Patent
DeFrees et al.

(10) Patent No.: US 7,368,108 B2
(45) Date of Patent: May 6, 2008

(54) GLYCOPEPTIDE REMODELING USING AMIDASES

(75) Inventors: Shawn DeFrees, North Wales, PA (US); Karl F. Johnson, Willow Grove, PA (US)

(73) Assignee: Neose Technologies, Inc., Horsham, PA (US)

(*) Notice: Subject to any disclaimer, the term of this patent is extended or adjusted under 35 U.S.C. 154(b) by 391 days.

(21) Appl. No.: 10/497,283

(22) PCT Filed: Nov. 27, 2002

(86) PCT No.: PCT/US02/38440

§ 371 (c)(1),
(2), (4) Date: Nov. 5, 2004

(87) PCT Pub. No.: WO03/045980

PCT Pub. Date: Jun. 5, 2003

(65) Prior Publication Data

US 2005/0118672 A1    Jun. 2, 2005

Related U.S. Application Data

(60) Provisional application No. 60/334,233, filed on Nov. 28, 2001.

(51) Int. Cl.
*A61K 38/51*    (2006.01)
*C12Q 1/48*    (2006.01)

(52) U.S. Cl. .............. 424/94.5; 435/15; 435/193; 435/252.3

(58) Field of Classification Search .......... 435/15, 435/193, 68.1, 69.1, 252.3; 424/94.5
See application file for complete search history.

(56) References Cited

U.S. PATENT DOCUMENTS

2002/0150981 A1    10/2002    Canfield

OTHER PUBLICATIONS

Kuhn et al. JBC 270(49): 29493-97, Dec. 1995.*
PNGase-F amidase sequence from F. meningosepticum (Registry Nos. 128688-70-0).*
PNGase-F amidase from F. meningosepticum (Registry Nos. 128688-71-1).*
Hayes et al. The Biosynthesis of Oligosaccharides in Intact Golgi Preparations From Rat Liver. Analysis of N-linked and O-Linked Glycans Labeled by UDP-[6-3H]N-Acetylgalactosamine. Journal Biol. Chem. Aug. 5, 1993 vol. 268, No. 22, pp. 16170-16178.

* cited by examiner

*Primary Examiner*—Tekchand Saidha
(74) *Attorney, Agent, or Firm*—Morgan, Lewis & Bockius, LLP

(57) ABSTRACT

This invention provides methods for modifying glycosylation patterns of glycopeptides, including recombinantly produced glycopeptides. Also provided are glycopeptide compositions in which the glycopeptides have a homogeneous glycosylation pattern.

33 Claims, 2 Drawing Sheets

SEQUENCE LISTING

<160> NUMBER OF SEQ ID NOS: 1

<210> SEQ ID NO 1
<211> LENGTH: 314
<212> TYPE: PRT
<213> ORGANISM: Flavobacterium meningosepticum

<400> SEQUENCE: 1

```
Ala Pro Ala Asp Asn Thr Val Asn Ile Lys Thr Phe Asp Lys Val Lys
 1               5                  10                  15

Asn Ala Phe Gly Asp Gly Leu Ser Gln Ser Ala Glu Gly Thr Phe Thr
            20                  25                  30

Phe Pro Ala Asp Val Thr Thr Val Lys Thr Ile Lys Met Phe Ile Lys
        35                  40                  45

Asn Glu Cys Pro Asn Lys Thr Cys Asp Glu Trp Asp Arg Tyr Ala Asn
50                  55                  60

Val Tyr Val Lys Asn Lys Thr Thr Gly Glu Trp Tyr Glu Ile Gly Arg
65                  70                  75                  80

Phe Ile Thr Pro Tyr Trp Val Gly Thr Glu Lys Leu Pro Arg Gly Leu
                85                  90                  95

Glu Ile Asp Val Thr Asp Phe Lys Ser Leu Leu Ser Gly Asn Thr Glu
            100                 105                 110

Leu Lys Ile Tyr Thr Glu Thr Trp Leu Ala Lys Gly Arg Glu Tyr Ser
        115                 120                 125

Val Asp Phe Asp Ile Val Tyr Gly Thr Pro Asp Tyr Lys Tyr Ser Ala
    130                 135                 140

Val Val Pro Val Ile Gln Tyr Asn Lys Ser Ser Ile Asp Gly Val Pro
145                 150                 155                 160

Tyr Gly Lys Ala His Thr Leu Gly Leu Lys Lys Asn Ile Gln Leu Pro
                165                 170                 175

Thr Asn Thr Glu Lys Ala Tyr Leu Arg Thr Thr Ile Ser Gly Trp Gly
            180                 185                 190

His Ala Lys Pro Tyr Asp Ala Gly Ser Arg Gly Cys Ala Glu Trp Cys
        195                 200                 205

Phe Arg Thr His Thr Ile Ala Ile Asn Asn Ala Asn Thr Phe Gln His
    210                 215                 220

Gln Leu Gly Ala Leu Gly Cys Ser Ala Asn Pro Ile Asn Asn Gln Ser
225                 230                 235                 240

Pro Gly Asn Trp Ala Pro Asp Arg Ala Gly Trp Cys Pro Gly Met Ala
                245                 250                 255

Val Pro Thr Arg Ile Asp Val Leu Asn Asn Ser Leu Thr Gly Ser Thr
            260                 265                 270

Phe Ser Tyr Glu Tyr Lys Phe Gln Ser Trp Thr Asn Asn Gly Thr Asn
        275                 280                 285

Gly Asp Ala Phe Tyr Ala Ile Ser Ser Phe Val Ile Ala Lys Ser Asn
    290                 295                 300

Thr Pro Ile Ser Ala Pro Val Val Thr Asn
305                 310
```

GLYCOPEPTIDE REMODELING USING AMIDASES

CROSS REFERENCE TO RELATED APPLICATIONS

The present application is a U.S. National Phase Application of PCT/US02/38440 filed Nov. 27, 2002, which claims priority from U.S. Provisional Application No. 60/334,233 filed Nov. 28, 2001, the disclosures of which are hereby incorporate by reference in their entirety.

BACKGROUND OF THE INVENTION

1. Field of the Invention

This invention pertains to the field of methods for remodeling glycopeptide to provide glycopeptides with novel and/or substantially uniform glycosylation patterns.

2. Background

A. Protein Glycosylation

The biological activity of many glycopeptides is highly dependent upon the presence or absence of particular oligosaccharide structures attached to the glycopeptide. Improperly glycosylated glycopeptides are implicated in cancer, infectious diseases and inflammation (Dennis et al., *BioEssays* 21: 412-421 (1999)). Moreover, the glycosylation pattern of a therapeutic glycopeptide can affect numerous aspects of the therapeutic efficacy such as solubility, resistance to proteolytic attack and thermal inactivation, immunogenicity, half-life, bioactivity, and stability (see, e.g., Rotondaro et al., *Mol. Biotechnol.* 11: 117-128 (1999); Lis et al., *Eur. J. Biochem.* 218: 1-27 (1993); Ono et al., *Eur. J. Cancer* 30A (Suppl. 3), S7-S11 (1994); and Hotchkiss et al., *Thromb. Haemost.* 60: 255-261 (1988)). Regulatory approval of therapeutic glycopeptides also requires that the glycosylation be homogeneous and consistent from batch to batch.

Glycosylation is a complex post-translational modification that is highly cell dependent. Following translation, proteins are transported into the endoplasmic reticulum (ER), glycosylated and sent to the Golgi for further processing. The resulting glycopeptides are subsequently targeted to various organelles, become membrane components, or they are secreted into the periplasm.

During glycosylation, either N-linked or O-linked glycopeptides are formed. N-glycosylation is a highly conserved metabolic process, which in eukaryotes is essential for viability. N-linked glycosylation is also implicated in development and homeostasis; N-linked glycopeptides constitute the majority of cell-surface proteins and secreted proteins, which are highly regulated during growth and development (Dennis et al., *Science* 236:582-585 (1987)). N-glycosylation is also believed to be related to morphogenesis, growth, differentiation and apoptosis (Kukuruzinska et al, *Biochem. Biophys. Acta.* (in press) (1998)).

In eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J.* 7:540-550 (1993); and Orlean, *Saccharomyces* Vol. 3 (1996)). O-linked glycosylation also takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995).

The biosynthesis of N-linked glycopeptides is initiated with the dolichol pathway in the endoplasmic reticulum (Burda, P., et al., *Biochimica et Biophysica Acta* 1426:239-257 (1999); Kornfeld et al., *Ann. Rev. Biochem.* 54:631-664 (1985); Kukuruzinska et al., *Ann. Rev. Biochem.* 56:915-944 (1987); Herscovics et al., *FASEB J.* 7:540-550 (1993)). At the heart of the dolichol pathway is the synthesis of an oligosaccharide linked to a polyisoprenol carrier lipid. The oligosaccharide, $GlcNAc_2Man_9Glc_3$, is assembled through the glycosyl-transferase catalyzed, stepwise addition of monosaccharides. The dolichol pathway is highly conserved between yeast and mammals.

After the assembly of the dolichol-oligosaccharide conjugate, the oligosaccharide is transferred from this conjugate to an asparagine residue of the protein consensus sequence. The transfer of the oligosaccharide is catalyzed by the multi-subunit enzyme oligosaccharyltransferase (Karaoglu et al., *Cold Spring Harbor Symposia on Quantitative Biology* LX:83-92 (1995b); and Silberstein et al., *FASEB J.* 10:849-858 (1996). Subsequent to the transfer of the oligosaccharide to the protein, a series of reactions, which shorten the oligosaccharide occur. The reactions are catalyzed by glucosidases I and II and α-mannosidase (Kilker et al., *J. Biol. Chem.*, 256:5299-5303 (1981); Saunier et al., *J. Biol. Chem.* 257:14155-14161 (1982); and Byrd et al., *J. Biol. Chem.* 257:14657-14666 (1982)).

Following the synthesis and processing of the N-linked glycopeptide in the endoplasmic reticulum, the glycopeptide is transported to the Golgi, where various processing steps result in the formation of the mature N-linked oligosaccharide structures. Although the dolichol pathway is highly conserved in eukaryotes, the mature N-linked glycopeptides produced in the Golgi exhibit significant structural variation across the species. For example, yeast glycopeptides include oligosaccharide structures that consist of a high mannose core of 9-13 mannose residues, or extended branched mannan outer chains consisting of up to 200 residues (Ballou, et al., *Dev. Biol.* 166:363-379 (1992); Trimble et al., *Glycobiology* 2:57-75 (1992). In higher eukaryotes, the N-linked oligosaccharides are typically high mannose, complex and mixed types of structures that vary significantly from those produced in yeast (Kornfeld et al., *Ann. Rev. Biochem.* 54:631-664 (1985)). Moreover, in yeast, a single α-1,2-mannose is removed from the central arm of the oligosaccharide, in higher eukaryotes, the removal of mannose involves the action of several mannosidases to generate a $GlcNAc_2Man_5$ structure (Kukuruzinska et al., *Crit Rev Oral Biol Med.* 9(4):415-448 (1998)). The branching of complex oligosaccharides occurs after the trimming of the oligosaccharide to the $GlcNAc_2Man_5$ structure. Branched structures, e.g. bi-, tri- and tetra-antennary, are synthesized by the GlcNAc transferase-catalyzed addition of GlcNAc to regions of the oligosaccharide residue. Subsequent to their formation, the antennary structures are terminated with different sugars including Gal, GalNAc, GlcNAc, Fuc and sialic acid residues.

Similar to N-glycosylation, O-glycosylation is also markedly different between mammals and yeast. At the initiation of O-glycosylation, mammalian cells add a GalNAc residue directly to Ser or Thr using UDP-GalNAc as a glycosyl donor. The saccharide unit is elongated by adding Gal, GlcNAc, Fuc and NeuNAc. In contrast to mammalian cells, lower eukaryotes, e.g., yeast and other fungi, add a mannose to Ser or Thr using Man-P-dolichol as a glycosyl donor. The saccharides are elongated by adding Man and/or Gal. See, generally, Gemmill et al., *Biochim. Biophys Acta* 1426: 227-237 (1999).

Efforts to elucidate the biological mechanism of protein glycosylation and the glycosylation patterns of glycopeptides had been aided by a number of analytical techniques. For example, N-linked oligosaccharides of recombinant aspartic protease were characterized using a combination of mass spectrometric, 2D chromatographic, chemical and enzymatic methods (Montesino et al., *Glycobiology* 9: 1037-1043 (1999)). The same workers have also reported the characterization of oligosaccharides enzymatically released from purified glycopeptides using fluorescent-labeled derivatives of the released oligosaccharides in combination with fluorophore-assisted carbohydrate electrophoresis (FACE) (Montesino et al., *Protein Expression and Purification* 14:197-207 (1998)).

Cloned endo- and exo-glycosidases are standardly used to release monosaccharides and N-glycans from glycopeptides. The endoglycosidases allow the discrimination between N-linked and O-linked glycans and between classes of N-glycans. Methods of separating glycopeptides on separated glycans have also become progressively more sophisticated and selective. Methods of separating mixtures of glycopeptides and cleaved glycans have also continued to improve and techniques such as high pH anion exchange chromatography (HPAEC) are routinely used for the separation of individual oligosaccharide isomers from a complex mixture of oligosaccharides. Recently, a large-scale organic solvent (acetone) precipitation-based method for isolating saccharides released from glycopeptides was reported by Verostek et al. (*Analyt. Biochem.* 278: 111-122 (2000). Many other methods of isolating and characterizing oligosaccharides released from glycopeptides are known in the art. See, generally, Fukuda et al., GLYCOBIOLOGY: A PRACTICAL APPROACH, Oxford University Press, New York 1993; and E. F. Hounsell (Ed.) GLYCOPEPTIDE ANALYSIS IN BIOMEDICINE, Humana Press, Totowa, N.J., 1993.

B. Synthesis of Glycopeptides

Considerable effort has been directed towards the identification and optimization of new strategies for the preparation of saccharides and glycopeptides derived from these saccharides. Included amongst the many promising methods are the engineering of cellular hosts that produce glycopeptides having a desired glycosylation pattern, chemical synthesis, enzymatic synthesis, enzymatic remodeling of formed glycopeptides and methods that are hybrids of one or more of these techniques.

Cell host systems have been investigated in which glycopeptides of interest as pharmaceutical agents can be produced in commercially feasible quantities. In principle, mammalian, insect, yeast, fungal, plant or prokaryotic cell culture systems can be used for production of most therapeutic and other glycopeptides. In practice, however, a desired glycosylation pattern on a recombinantly produced protein is difficult to achieve. For example, bacteria do not N-glycosylate via the dolichol pathway, and yeast make only oligomannose-type N-glycans, which are not generally found in humans. (see, e.g., Ailor et al. *Glycobiology* 1: 837-847 (2000)). Similarly, plant cells do not produce sialylated oligosaccharides, a common constituent of human glycopeptides (see, generally, Liu, *Trends Biotechnol* 10: 114-20 (1992); and Lerouge et al., *Plant Mol. Biol.* 38: 31-48 (1998)). As recently reviewed, none of the insect cell systems presently available the production of recombinant mammalian glycopeptides will produce glycopeptides with the same glycans normally found when they are produced in mammals. Moreover, glycosylation patterns of recombinant glycopeptides frequently differ when they are produced under different cell culture conditions (Watson et al. *Biotechnol. Prog.* 10: 39-44 (1994); and Gawlitzek et al., *Biotechnol. J.* 42: 117-131 (1995)). It now appears that glycosylation patterns of recombinant glycopeptides can vary between glycopeptides produced under nominally identical cell culture conditions in two different bioreactors (Kunkel et al., *Biotechnol. Prog.* 2000:462-470 (2000). Finally, in many bacterial systems, the recombinantly produced proteins are completely unglycosylated.

Heterogeneity in the glycosylation of a recombinantly produced glycopeptides arises because the cellular machinery (e.g., glycosyltransferases and glycosidases) may vary from species to species, cell to cell, or even from individual to individual. The substrates recognized by the various enzymes may be sufficiently different that glycosylation may not occur at some sites or may be vastly modified from that of the native protein. Glycosylation of recombinant proteins produced in heterologous eukaryotic hosts will often differ from the native protein. For example, yeast and insect expressed glycopeptides typically contain high mannose structures that are not commonly seen in humans.

An area of great interest is the design of host cells that have the glycosylation apparatus necessary to prepare properly glycosylated recombinant human glycopeptides. The Chinese hamster ovary (CHO) cell is a model cell system that has been particularly well studied, because CHO cells are equipped with a glycosylation machinery that is very similar to that found in the human (Jenkins et al., *Nature Biotechnol.* 14: 975-981 (1996)). In contrast to the many similarities between the glycosylation patterns of glycopeptides from human cells and those from CHO cells, an important distinction exists; glycopeptides produced by CHO cells carry only α-2,3-terminal sialic acid residues, whereas those produced by human cells include both α-2,3- and α-2,6-terminal sialic acid residues (Lee et al., *J. Biol. Chem.* 264: 13848-13855 (1989)).

Efforts to remedy the deficiencies of the glycosylation of a particular host cell have focused on engineering the cell to express one or more missing enzymes integral to the human glycosylation pathway. For example, Bragonzi et al. (*Biochim. Biophys. Acta* 1474: 273-282 (2000)) have produced a CHO cell that acts as a 'universal host' cell, having both α-2,3- and α-2,6-sialyltransferase activity. To produce the universal host, CHO cells were transfected with the gene encoding expression of α-2,6-sialyltransferase. The resulting host cells then underwent a second stable transfection of the genes encoding other proteins, including human interferon γ (IFN-γ). Proteins were recovered that were equipped with both α-2,3- and α-2,6-sialic acid residues. Moreover, in vivo pharmacokinetic data for IFN-γ demonstrate improved pharmacokinetics of the IFN-γ produced by the universal host, as compared to the IFN-γ secreted by regular CHO cells transfected with IFN-γ cDNA. A similar study is reported by Weikert et al. (*Nature Biotechnology* 17: 1116-35 U.S.C. § 112, first paragraph (1999).

In addition to preparing properly glycosylated glycopeptides by engineering the host cell to include the necessary compliment of enzymes, efforts have been directed to the development of both de novo synthesis of glycopeptides and the in vitro enzymatic methods of tailoring the glycosylation of glycopeptides. Methods of synthesizing both O-linked and N-linked glycopeptides have been recently reviewed (Arsequell et al., *Tetrahedron: Assymetry* 8: 2839 (1997); and Arsequell et al., *Tetrahedron: Assymetry* 10: 2839 (1997), respectively).

Two broad synthetic motifs are used to synthesize N-linked glycopeptides: the convergent approach; and the stepwise building block approach. The stepwise approach generally makes use of solid-phase peptide synthesis methodology, originating with a glycosyl asparagine intermediate. In the convergent approach, the peptide and the carbohydrate are assembled separately and the amide linkage between these two components is formed late in the synthesis. Although great advances have been made in recent years in both carbohydrate chemistry and the synthesis of glycopeptides, there are still substantial difficulties associated with chemical synthesis of glycopeptides, particularly with the formation of the ubiquitous β-1,2-cis-mannoside linkage found in mammalian oligosaccharides. Moreover, regio- and stereo-chemical obstacles must be resolved at each step of the de novo synthesis of a carbohydrate. Thus, this field of organic synthesis lags substantially behind the de novo synthesis of other biomolecules such as oligonucleotides and peptides.

In view of the difficulties associated with the chemical synthesis of carbohydrates, the use of enzymes to synthesize the carbohydrate portions of glycopeptides is a promising approach to preparing glycopeptides. Enzyme-based syntheses have the advantages of regioselectivity and stereoselectivity. Moreover, enzymatic syntheses can be performed using unprotected substrates. Three principal classes of enzymes are used in the synthesis of carbohydrates, glycosyltransferases (e.g., sialyltransferases, oligosaccharyltransferases, N-acetylglucosaminyltransferases), glycoaminidases (e.g., PNGase F) and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., *Curr. Opin. Chem. Biol.* 2:98-111 (1998) and Arsequell, supra.

Glycosyltransferases have been used to modify the oligosaccharide structures on glycopeptides. Glycosyltransferases have been shown to be very effective for producing specific products with good stereochemical and regiochemical control. Glycosyltransferases have been used to prepare oligosaccharides and to modify terminal N- and O-linked carbohydrate structures, particularly on glycopeptides produced in mammalian cells. For example, the terminal oligosaccharides have been completely sialylated and/or fucosylated to provide more consistent sugar structures which improves glycopeptide pharmacodynamics and a variety of other biological properties. For example, β-1,4-galactosyltransferase was used to synthesize lactosamine, the first illustration of the utility of glycosyltransferases in the synthesis of carbohydrates (see, e.g., Wong et al., *J. Org. Chem.* 47: 5416-5418 (1982)). Moreover, numerous synthetic procedures have made use of α-sialyltransferases to transfer sialic acid from cytidine-5'-monophospho-N-acetylneuraminic acid to the 3-OH or 6-OH of galactose (see, e.g., Kevin et al., *Chem. Eur. J.* 2: 1359-1362 (1996)). For a discussion of recent advances in glycoconjugate synthesis for therapeutic use see, Koeller et al., *Nature Biotechnology* 18: 835-841 (2000).

Glycosidases normally catalyze the hydrolysis of a glycosidic bond, however, under appropriate conditions they can be used to form this linkage. Most glycosidases used for carbohydrate synthesis are exoglycosidases; the glycosyl transfer occurs at the non-reducing terminus of the substrate. The glycosidase takes up a glycosyl donor in a glycosyl-enzyme intermediate that is either intercepted by water to give the hydrolysis product, or by an acceptor, to give a new glycoside or oligosaccharide. An exemplary pathway using a exoglycoside is the synthesis of the core trisaccharide of all N-linked glycopeptides, including the notoriously difficult β-mannoside linkage, which was formed by the action of β-mannosidase (Singh et al., *Chem. Commun.* 993-994 (1996)).

Fucosyltransferases have been used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)).

Although their use is less common than that of the exoglycosidases, endoglycosidases have also been utilized to prepare carbohydrates. Methods based on the use of endoglycosidases have the advantage that an oligosaccharide, rather than a monosaccharide, is transferred. Oligosaccharide fragments have been added to substrates using endo-β-N-acetylglucosamines such as endo-F, endo-M (Wang et al., *Tetrahedron Lett.* 37: 1975-1978); and Haneda et al., *Carbohydr. Res.* 292: 61-70 (1996)).

In addition to their use in the preparing carbohydrates, the enzymes discussed above have been applied to the synthesis of glycopeptides as well. The synthesis of a homogenous glycoform of ribonuclease B has been published (Witte K. et al., *J. Am. Chem. Soc.* 119: 2114-2118 (1997)). The high mannose core of ribonuclease B was cleaved by treating the glycopeptide with endoglycosidase H. The cleavage occurred specifically between the two core GlcNAc residues. The tetrasaccharide sialyl Lewis X was then enzymatically rebuilt on the remaining GlcNAc anchor site on the now homogenous protein by the sequential use of β-1,4-galactosyltransferase, α-2,3-sialyltransferase and α-1,3-fucosyltransferase V. Each enzymatically catalyzed step proceeded in excellent yield.

Methods combining both chemical and enzymatic synthetic elements are also known. For example, Yamamoto and coworkers (*Carbohydr. Res.* 305: 415-422 (1998)) reported the chemoenzymatic synthesis of the glycopeptide, glycosylated Peptide T, using an endoglycosidase. The N-acetylglucosaminyl peptide was synthesized by purely chemical means. The peptide was subsequently enzymatically elaborated with the oligosaccharide of human transferrin glycopeptide. The saccharide portion was added to the peptide by treating it with an endo-β-N-acetylglucosaminidase. The resulting glycosylated peptide was highly stable and resistant to proteolysis when compared to the peptide T and N-acetylglucosaminyl peptide T.

In conjunction with the interest in the use of enzymes to form and remodel glycopeptides, there is interest in producing enzymes that are engineered to produce desired glycosylation patterns. Methods of producing and characterizing mutations of enzymes of use in producing glycopeptides have been reported. For example, Rao et al. (*Protein Science* 8:2338-2346 (1999) have prepared mutants of endo-β-N-acetylglucosaminidase that are defined by structural changes, which reduce substrate binding and alter the enzyme functionality. Withers et al. (U.S. Pat. No. 5,716,812) have prepared mutant glycosidase enzymes in which the normal nucleophilic amino acid within the active site has been changed to a non-nucleophilic amino acid. The mutated enzymes cannot hydrolyze disaccharide products, but can still form them.

The overall structure and the structure of the active site of both mutated and native enzymes have been characterized by x-ray crystallography. See, e.g., van Roey et al., *Biochemistry* 33: 13989-13996 (1994); and Norris et al., *Structure* 2: 1049-1059 (1994).

Despite the many advantages of the enzymatic synthesis methods set forth above, in some cases, deficiencies remain. The preparation of properly glycosylated glycopeptides is an exemplary situation in which additional effort is required and effort is being directed to improving both the synthesis of glycopeptides and methods of remodeling biologically or chemically produced glycopeptides that are not properly glycosylated. To realize the potential of enzymatic oligosaccharide and glycopeptide synthesis and glycopeptide remodeling, there is a need for new synthetic approaches. Since the biological activity of many commercially important recombinantly and transgenically produced glycopeptides depends upon the presence or absence of a particular glycoform, a need exists for an in vitro procedure to enzymatically modify glycosylation patterns on such glycopeptides. The present invention fulfills these and other needs.

SUMMARY OF THE INVENTION

The present invention provides methods of remodeling the N-linked glycosylation pattern of a glycopeptide. Typically, the methods are carried out by glycosylating a polypeptide which comprises an Asn or an Asp residue. The protein will generally be recombinantly produced and may be first treated chemically or with an appropriate enzyme (e.g.,endoglycanase, amidase or protease) to remove existing N-linked carbohydrate structure. The method can also utilize one or more steps in which an appropriate acceptor moiety is ligated onto the peptide structures. The methods of the invention include contacting the polypeptide with an activated glycosyl donor molecule (e.g., a species having a leaving group) under conditions suitable for linking the activated GlcNAc residue on the glycosyl donor molecule to an Asn or Asp residue on the polypeptide. If desired, the glycosylation pattern of the peptide produced using the method of the invention can be further elaborated using glycosylation according to the methods set forth herein, or known in the art.

The mutant amidase typically includes a substitution of an amino acid residue for an active site acidic amino acid residue. For example, when the amidase is PNGase-F, the substituted active site residues will typically be Asp at position 60, Glu at position 206 or Glu at position 118.

The mutant enzyme catalyzes the reaction, usually by either of two pathways. In one pathway, the synthesis step is the reverse reaction of the amidase hydrolysis step. In these embodiments, the glycosyl donor molecule (e.g., a desired oligo- or mono-saccharide structure) contains a leaving group and the reaction proceeds with the addition of the donor molecule to an Asp residue on the protein. In the second pathway, the reaction proceeds with addition of the glycosyl donor to Asn residues of the protein. In these embodiments, the glycosyl donor molecule is typically modified with a leaving group at the reducing terminus of the molecule. For example, the leaving group can be a halogen, such as fluoride. In other embodiments the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

The particular glycosyl donor molecule used in the methods of the invention is not a critical aspect of the invention. Any desired carbohydrate structure can be added to a glycopeptide using the methods of the invention and can be controlled to some extent depending on the substrate specificity of the glycosidase utilized. Typically, the structure will comprise a bi, tri, or tetra-antennary structure commonly found on human glycopeptides.

The acceptor glycopeptide is also not a critical aspect of the invention. Typically, the glycopeptide will be recombinantly expressed in a prokaryotic cell (e.g., bacterial cell, such as *E coli*) or in a eukaryotic cell such as a mammalian, yeast, insect, fungal or plant cell. The glycopeptide can be either a full length protein or a fragment. In some embodiments, the glycopeptide can be reversibly attached to solid support, according to well known techniques.

The invention also provides glycopeptides in which the glycosylation pattern is remodeled according to the method of the invention. Typically, at least 40% of the acceptor moieties, preferably at least about 60% and often at least about 80% of the targeted acceptor moieties on the glycopeptide are glycosylated. In some embodiments, the glycopeptide is reversibly immobilized on a solid support, such as an affinity chromatography medium.

The present invention also provides methods for producing glycopeptides that have a glycosylation pattern, which is substantially identical to the glycosylation pattern of a known glycopeptide. The method includes contacting a peptide or glycopeptide having an acceptor for a mutant amidase of the invention with a glycosyl donor and the mutant amidase. The transfer of the glycosyl donor onto the peptide or glycopeptide is terminated upon reaching a desired level of glycosylation. Among the uses of this aspect of the invention is the duplication of therapeutically relevant glycopeptide structures that have been approved or are nearing approval by a regulatory agency for use in humans. Thus, although a more (or less) thoroughly glycosylated peptide might have improved properties, the ability to duplicate an already approved glycopeptide structure obviates the necessity of submitting certain glycopeptides prepared by the instant method to the full regulatory review process, thereby providing an important economic advantage. This would allow switching from a production cell line with adequate glycosylation capabilities, but limited in expression level, to a production cell line that has the capability of producing significantly greater amounts of product, but yielding an inferior glycosylation pattern. The glycosylation pattern can then be modified in vitro to match that of the desired product. The yield of desired glycosylated product may then be increased substantially for a given bioreactor size, impacting both production economics and plant capacity. The particular glycopeptide used in the methods of the invention is generally not a critical aspect of the invention. The glycopeptide may be a fragment or a full-length glycopeptide. Typically, the glycopeptide is one that has therapeutic use such as a hormone, a growth factor, an enzyme inhibitor, a cytokine, a receptor, a IgG chimera, or a monoclonal antibody.

Also provided are methods for the large-scale production of glycosylated glycopeptides having a substantially uniform glycosylation pattern, and large-scale methods for producing glycopeptides having a known glycosylation pattern using a mutant amidase of the invention.

The invention also provides compositions comprising the glycopeptides prepared by the methods of the invention, and methods of using the composition in therapy and diagnosis.

Additional objects and advantages of the present invention will be apparent from the detailed description that follows.

DETAILED DESCRIPTION OF THE INVENTION AND THE PREFERRED EMBODIMENTS

Definitions

Figure 1:
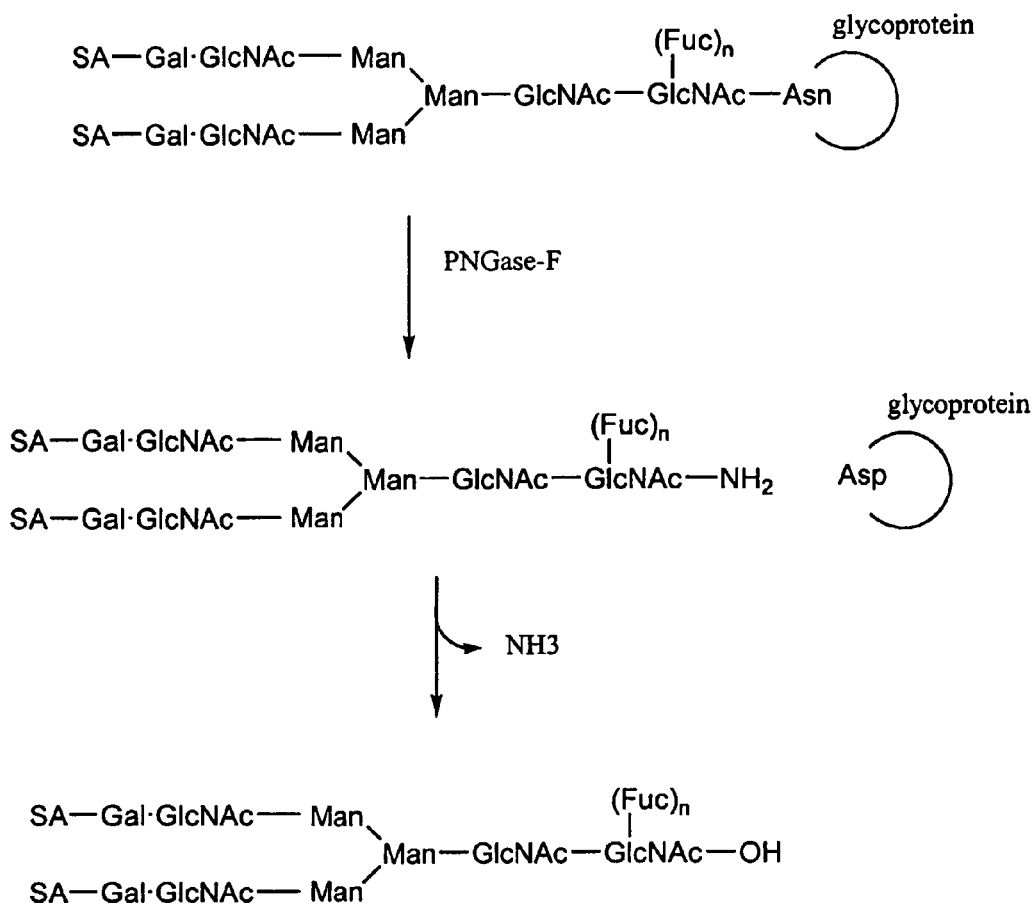
FIG. 1 shows exemplary oligosaccharides that can be added to proteins using the methods of the invention.

The following abbreviations are used herein:
Ara=arabinosyl;
Fru=fructosyl;
Fuc=fucosyl;
Gal=galactosyl;
GalA=galacturonyl;
GalNAc=N-acetylgalactosaminyl;
Glc=glucosyl;
GlcNAc=N-acetylglucosaninyl;
Man=mannosyl;
NeuAc=N-acetylneuraminyl.
NeuGc=N-glycolylneuraminyl;
Xyl=xylosyl.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond ($\alpha$ or $\beta$), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O-$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

As used herein, the term "mutant amidase", refers to an amidase of the present invention. Exemplary mutant amidases are produced recombinantly, however, the invention also includes the use of mutant amidases produced by chemical methods of mutation and also by synthesis of all or a portion of an amidase peptide sequence. Preferred mutant amidases lack a membrane anchoring region.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant polypeptide" is one which has been produced by a recombinant cell.

A "heterologous sequence" or a "heterologous nucleic acid", as used herein, is one that originates from a source foreign to the particular host cell, or, if from the same source, is modified from its original form. Thus, a heterologous glycopeptide gene in a eukaryotic host cell includes a glycopeptide gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "altered" refers to a peptide having a glycosylation pattern that, after application of the methods of the invention, is different from that observed on the peptide as originally produced, e.g., expressed. Typically, the oligosaccharide structures on the originally produced peptide are first removed by a wild-type amidase or endoglycanase and then replaced by a desired structure or structures using the methods of the invention.

"Peptide" and "polypeptide" are used interchangeably to refer to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" and "polypeptide" refer to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a marner similar to a naturally occurring amino acid.

"Known glycosylation pattern," refers to a glycosylation pattern of a known glycopeptide from any source having any known level of glycosylation.

The term "isolated" refers to a material that is substantially or essentially free from components, which are used to produce the material. For glycopeptides of the invention, the term "isolated" refers to material that is substantially or essentially free from components, which normally accompany the material in the mixture used to prepare the glycopeptide. "Isolated" and "pure" are used interchangeably. Typically, isolated glycopeptides of the invention have a level of purity preferably expressed as a range. The lower end of the range of purity for the glycopeptides is about 60%, about 70% or about 80% and the upper end of the range of purity is about 70%, about 80%, about 90% or more than about 90%.

When the glycopeptides are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of glycopeptides of the invention in which a selected percentage of the glycosyl donor moieties added to the peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the glycosyl donor moieties are conjugated. Thus, in a glycopeptide of the invention in which each glycosyl donor moiety is conjugated to an acceptor site having the same structure as the acceptor site to which every other glycosyl donor is conjugated, the glycopeptide is the to be about 100% homogeneous. Homogeneity is typically expressed as a range. The lower end of the range of homogeneity for the glycopeptides is about 60%, about 70% or about 80% and the upper end of the range of purity is about 70%, about 80%, about 90% or more than about 90%.

When the glycopeptides are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the glycopeptides is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyl donor of interest. For example, in the case of a mutant Endo-F3, a substantially unifomn fucosylation pattern exists if substantially all (as defined below) of the GlcNAc-Asn moieties are glycosylated in a glycopeptide of the invention. It is understood by one of skill in the art, that the starting material may contain glycosylated acceptor moieties that are glycosylated with a species having the same structure as the glycosyl donor (typically without the leaving group). Thus, the calculated percent glycosylation includes acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular mutant amidase or glycosyltransferase are glycosylated.

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology,* F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, eukaryotic cells including insect, mammalian, plant, yeast, and fungal cells.

The Methods

Glycopeptides that have modified glycosylation patterns have important advantages over proteins that are in a glycosylation state that is less than optimal for a particular application. Such non-optimal glycosylation patterns can arise when a recombinant glycopeptide is produced in a cell that does not have the proper complement of glycosylation machinery to produce the desired glycosylation pattern. The optimal or preferred glycosylation pattern may or may not be the native glycosylation pattern of the glycopeptide when produced in its native cell.

The biological activity of many glycopeptides depends upon the presence or absence of a particular glycoform; thus the methods of the invention are useful for obtaining a composition of a glycopeptide that has an increased level of a desired biological activity compared to the glycopeptide prior to application of the methods of the invention. For example, increased glycosylation at an acceptor moiety will render a glycopeptide highly multivalent, thereby increasing the biological activity of the glycopeptide. Other advantages of glycopeptide compositions that have desired glycosylation patterns include, for example, increased therapeutic half-life of a glycopeptide due to reduced clearance rate. Altering the glycosylation pattern can also mask antigenic determinants on foreign proteins, thus reducing or eliminating an immune response against the protein. Alteration of the glycoform of a glycopeptide-linked saccharide can also be used to target a protein to a particular tissue or cell surface receptor that is specific for the desired oligosaccharide. The desired oligosaccharide can also be used to inhibit interactions between a receptor and its natural ligand.

In contrast to known chemical and enzymatic peptide elaboration strategies, the methods of the invention, make it possible to assemble peptides and glycopeptides that have a substantially homogeneous derivatization pattern. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fimgal cells, yeast cells, or prokaryotic cells) or transgenic plants or animals.

In a first aspect, the invention provides a method for modifying the glycosylation pattern of a polypeptide comprising an acceptor moiety for a first mutant amidase. The method includes contacting the polypeptide with a reaction mixture that comprises a glycosyl donor moiety and the first mutant amidase under appropriate conditions to transfer a glycosyl residue from the glycosyl donor moiety to the acceptor moiety, such that the resulting glycopeptide has a substantially uniform glycosylation pattern.

In another aspect, the present invention provides method for preparing industrially relevant quantities of peptides having a selected glycosylation pattern. Thus, there is provided a large-scale method for modifying the glycosylation pattern of a polypeptide that includes an acceptor moiety for a mutant amidase. The method includes contacting at least about 500 mg of the polypeptide with a reaction mixture that includes a glycosyl donor moiety for the mutant amidase and the mutant amidase under conditions appropriate to transfer a glycosyl residue from the glycosyl donor moiety to the acceptor moiety, thereby producing the glycopeptide having the modified glycosylation pattern.

In yet a further aspect, the invention provides a large scale method for preparing a peptide that has a glycosylation pattern that is substantially identical to that of a known glycopeptide. In an example of this aspect, the method includes contacting at least about 500 mg of a polypeptide with a reaction mixture that comprises a glycosyl donor moiety and a mutant amidase under conditions appropriate to transfer a glycosyl residue from the glycosyl donor moiety to a glycosyl acceptor moiety on the polypeptide. The reaction is allowed to proceed for a preselected period of time and is then terminated when the glycosylation pattern is substantially identical to the known glycosylation pattern is obtained.

The invention provides compositions that include glycopeptide species that have a substantially uniform N-linked glycosylation pattern. Methods and kits for obtaining such compositions are also provided. The methods of the invention are useful for remodeling or altering the glycosylation pattern present on a peptide or glycopeptide upon its initial expression.

The methods of the invention provide compositions of glycopeptides that have a substantially uniform glycosylation pattern. The methods are also practical for large-scale production of modified glycopeptides. Thus, the methods of the invention provide a practical means for large-scale preparation of glycopeptides having desired glycosylation patterns. The methods are well suited for modification of therapeutic glycopeptides that are incompletely glycosylated during production in cell culture cells (e.g., mammalian cells, insect cells, plant cells, fungal cells, yeast cells, or prokaryotic cells) or transgenic plants or animals. Moreover, the methods are of general utility for converting a non-human glycoform to a human glycoforn. Further, the methods can be used to conjugate a carbohydrate having a particular property (e.g., tissue targeting, enhancing in vivo residence, etc.) onto a peptide. The processes provide an increased and consistent level of a desired N-linked glycoform on glycopeptides present in a composition.

In an exemplary embodiment, the method of the invention further includes contacting a polypeptide with a glycosyltransferase in addition to a mutant amidase. For example, in one embodiment, the polypeptide comprises an acceptor moiety for a glycosyltransferase. The method further includes contacting the polypeptide with a reaction mixture that comprises a glycosyl donor moiety and the glycosyltransferase under appropriate conditions to transfer a glycosyl residue from the glycosyl donor moiety to the acceptor moiety. In a preferred embodiment, the resulting polypeptide has a substantially uniform glycosylation pattern. In yet another preferred embodiment, the glycosyltransferase is selected from fucosyltransferases, sialyltransferases and combination thereof In those embodiments in which one or more glycosyltransferase is utilized in addition to the mutant amidase, the precursor peptide or glycopeptide may be contacted with one or more glycosyltransferases substantially simultaneously. Alternatively, the precursor peptide or glycopeptide is contacted with one or more glycosyltransferase and the mutant amidase substantially simultaneously. The method of the invention optionally consists of two or more individual steps utilizing one or more enzyme.

The methods of the invention are practiced successfully with substantially any peptide or glycopeptide. When the peptide or glycopeptide does not include an appropriate acceptor moiety, it is within the scope of the present invention to add the appropriate moiety by enzymatic and/or chemical methods. The methods of the invention generally provide a pure, homogeneous glycopeptide that is characterized by a substantially uniform glycosylation pattern.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment.

The method of the invention also provides for modification of incompletely glycosylated peptides that are produced recombinantly. Many recombinantly produced glycopeptides are incompletely glycosylated, exposing carbohydrate residues that may have undesirable properties, e.g., immunogenicity, recognition by the RES. Exemplary peptides that can be modified using the methods of the invention are set forth in Table 1.

TABLE 1

Hormones and Growth Factors

G-CSF
GM-CSF
TPO
EPO
EPO variants
NESP
alpha-TNF
Leptin

Enzymes and Inhibitors t-PA
t-PA variants
Urokinase
Factors VII, VIII, IX, X
Dnase
Glucocerebrosidase
Alpha-glucosidase
iduronidase
Hirudin
α1 antitrypsin
Antithrombin III Cytokines and Chimeric Cytokines Interleukin-1 (IL-1), 1B, 2, 3, 4
Interferon-alpha (IFN-alpha)
IFN-alpha-2a or b
IFN-beta
IFN-gamma
IFN-omega
Chimeric diptheria toxin-IL-2

Receptors and Chimeric Receptors

CD4
Tumor Necrosis Factor (TNF) receptor
Alpha-CD20
MAb-CD20
MAb-alpha-CD3
MAb-TNF receptor
MAb-CD4

TABLE 1-continued

PSGL-1
MAb-PSGL-1
Complement
GlyCAM or its chimera
N-CAM or its chimera

Monoclonal Antibodies (Immunoglobulins)

MAb-anti-RSV
MAb-anti-IL-2 receptor
MAb-anti-CEA
MAb-anti-platelet IIb/IIIa receptor
MAb-anti-EGF
MAb-anti-Her-2 receptor
Remicade Cells Red blood cells
White blood cells (e.g., T cells, B cells,
dendritic cells, macrophages, NK cells,
neutrophils, monocytes and the like
Stem cells Other exemplary peptides that are modified by the methods of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (t-PA), renin, clotting factors such as factor VIII and factor IX, bombesin, thrombin, hematopoietic growth factor, colony stimulating factors, viral antigens, complement proteins, α1-antitrypsin, erythropoietin, P-selectin glycopeptide ligand-1 (PSGL-1), granulocyte-macrophage colony stimulating factor, anti-thrombin III, interleukins, interferons, proteins A and C, fibrinogen, herceptin, leptin, glycosidases, among many others. This list of polypeptides is exemplary, not exclusive. The methods are also useful for modifying chimeric proteins, including, but not limited to, chimeric proteins that include a moiety derived from an immunoglobulin, such as IgG. Still further exemplary peptides, which can be modified by the methods of the invention are set forth in Appendix 1.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although 5-hydroxyproline or 5-hydroxylysine may also be used.

Moreover, in addition to peptides, the methods of the present invention can be practiced with other biological structures (e.g., whole cells, and the like).

In certain embodiments, a glycosylation site not present in the wild type peptide is added to the peptide upon which the method of the invention is practiced. Addition of glycosylation sites to a peptide is conveniently accomplished by altering the amino acid sequence such that it contains one or more glycosylation sites. The addition may also be made by the incorporation of one or more species presenting an carboxyl or carboxyamide group, preferably aspartic acid or asparagine, within the sequence of the peptide (for N-linked glycosylation site). For ease, the peptide amino acid sequence is preferably altered through changes at the DNA level, particularly by mutating the DNA encoding the peptide at preselected bases such that codons are generated that will translate into the desired amino acids. The DNA mutation (s) are preferably made using methods known in the art.

Addition or removal of any carbohydrate moieties present on the peptide or glycopeptide is accomplished either chemically or enzymatically. Chemical deglycosylation is preferably brought about by exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of amidases and endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residues include, but are not limited to: (a) consensus sites for N- and O-glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

The glycosylation pattern of immunoglobulins, as well as chimeric proteins that include all or part of an immunoglobulin, such as an immunoglobulin heavy chain constant region, also affects biological activity. Oligosaccharides attached to IgG molecules purified from human sera, in particular the oligosaccharides attached to Asn297 of IgG, are important for IgG structure and function (Rademacher and Dwek (1983). *Prog. Immunol* 5: 95-112; Jefferies et al. (1990)). The absence of these oligosaccharides results in a lack of binding to the monocyte Fc receptor, a decline in complement activation, an increase in susceptibility to proteolytic degradation, and reduced clearance from circulation of antibody-antigen complexes. Immunoglobulin oligosaccharides, in particular those of IgG, naturally exhibit high microheterogeneity in their structures (Kobata (1990) *Glycobiology* 1: 5-8). Therefore, use of the methods of the invention to provide a more uniform glycopeptide results in an improvement of one or more of these biological activities (e.g. enhanced complement activation, increased binding to the monocyte Fc receptor, reduced proteolysis, and increased clearance of antibody-antigen complexes). The methods of the invention are also useful for modifying oligosaccharides on other immunoglobulins to enhance one or more biological activities. For example, high-mannose oligosaccharides are generally attached to IgM and IgD. Such oligosaccharides can be modified as described herein to yield antibodies with enhanced properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. As will be apparent to those of skill in the art, in this method, asparagine is optionally replaced by aspartic acid. O-linked glycosylation refers to the attachment of one sugar (e.g., N-acetylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

Moreover, in addition to peptides, the methods of the present invention can be practiced with other biological structures (e.g., whole cells, and the like).

The present invention is also useful in conjunction with methods that graft a glycosylation site onto a peptide at a location that does not have such a site upon expression. Addition of glycosylation sites to a peptide is conveniently accomplished by altering the amino acid sequence such that it contains one or more glycosylation sites. The addition may also be made by the incorporation of one or more species presenting an —$NH_2$ group, preferably Arg or Asn residues, within the sequence of the peptide (for $NH_2$-linked glycosylation sites). An Asp can also be used. For ease, the peptide amino acid sequence is preferably altered through changes at the DNA level, particularly by mutating the DNA encoding the peptide at preselected bases such that codons are generated that will translate into the desired amino acids. The DNA mutation (s) are preferably made using methods known in the art.

The present invention also provides means of adding one or more selected glycosyl residues to a peptide, either before or after the amidase has conjugated a carbohydrate to at least one of the selected amino acid residues of the peptide. The present embodiment is useful, for example, when it is desired to conjugate a carbohydrate moiety to a selected glycosyl residue that is either not present on a peptide or is not present on the peptide in a desired amount. Thus, prior to coupling a donor carbohydrate moiety to a peptide, the acceptor glycosyl residue is conjugated to the peptide by enzymatic or chemical coupling. In another embodiment, the glycosylation pattern of a glycopeptide is altered prior to the conjugation of the donor carbohydrate moiety by the removal of a carbohydrate residue from the glycopeptide to form a desired acceptor moiety. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved. See, e.g., U.S. Pat. Nos. 5,876,980, 6,030,815, 5,728,554, and 5,922,577.

Exemplary attachment points for selected glycosyl residue include, but are not limited to: (a) consensus sites for N- and O-glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

The methods of the invention use mutant amidases to add glycosidic linkages to asparagine or aspartic acid residues on glycopeptides. The mutant amidases are derived from amidases capable of cleaving the C—N bond of the glycosylated asparagine side chain, converting the asparagine to aspartic acid and liberating ammonia and the attached glycan. Examples of amidases useful in the invention include peptide-$N_4$-(N-acetyl-$\beta$-glucosaminyl)asparagine amidases (EC 3.5.1.52). Example of this class of enzyme include peptide: N-glycosidase F (PNGase F) derived from *Flavobacterium meningosepticum* (Tarentino et al. J. Biol. Chem. 265:6961-6966 (1990); APADNTVNIKTFDKVKNAFGDGLSQ-SAEGTFTFPADVTTVKTIKMFIKNECPNKTC DEW-DRYANVYVKNKTTGEWYEIGRFITPYWVGTEKLPR-GLEIDVTDFKSLLSGNT ELKIYETWLAKGREYSVD-FDIVYGTPDYKYSAVVPVIQYNKSSIDGVPYGKAHTL GLKKNIQLPTNTEKAYLRTTISGWGHAK-PYDAGSRGCAEWCFRTHTIAINNANTF QHQLGAL-GCSANPINNQSPGNWAPDRAGWCPG-MAVPTRIDVLNNSLTGSTFSYEY KFQSWTNNGTNGDAFYAISSFVIAKSNTPISAPVVTN (SEQ ID NO:01)), and almond emulsin peptide:N-glycosidase (PNGase-A). (Plummer et al. *J. Biol. Chem.* 256 (1981) 10243-10246 (1981)). Usually, the peptide linkage that is recognized by these enzymes includes Sugar-Asn-X-Ser (Thr)- or Asp-X-Ser (Thr) which is the normal peptide consensus sequence recognized by enzymes that introduce N-linked sugars through a cells normal biosynthetic pathway.

Other enzymes with similar activity that can also be used in the present invention include glycosylasparaginases (N4)-α-N-acetylglucosaminyl)-L-asparaginases, EC 3.5.1.26) such as mammalian or plant lysosomal glycosylasparaginases or bacterial glycosylaspariginases (see, Tollersrud et al. *Biochem.* 282:891-897 (1992) and Tarentino et al. *Biochem. Biophys. Res. Commun.* 197:179-186 (1993)).

The present invention is based on the observation that amidases such as those described above can be converted from a degradative enzyme to a synthetic enzyme. The change in the catalytic activity is induced by modifying amino acid residues of the enzyme to facilitate this conversion. Thus modified, the enzyme is able to add more product to the glycopeptide than it cleaves. Point mutations as well as entire peptide substitutions can be used to improve the synthetic capabilities of the enzyme. Typically these enzymes have two or more carboxylic acid groups in the active site of the enzyme. The present invention provides mutant forms of the enzymes noted above in which one or more of the carboxylic acid amino acids in the active site have been replaced with a different amino acid. Such mutations provide enzymes which do not catalyze the hydrolysis of oligosaccharides, but which nevertheless retain activity to synthesize oligosaccharides with good control over the stereochemistry and regiochemistry of the reaction.

Thus, in general, the substitution will involve replacing a glutamic acid or aspartic acid residue of the wild-type enzyme with alanine, glycine, valine, leucine, isoleucine, serine, threonine, cysteine, methionine, asparagine, glutamine, histidine, proline, phenylalanine, or tyrosine. Preferably, the substituted amino acid will have a side chain of approximately equal or smaller size to the side chain of the wild-type amino acid residue to avoid significant changes to the size and shape of the active site. Enzymes mutated in this way are inactive with the normal substrates, and thus cannot hydrolyze oligosaccharide products. They can, however, catalyze the coupling of modified glycosyl donor molecules to modified acceptors.

Figure 2:
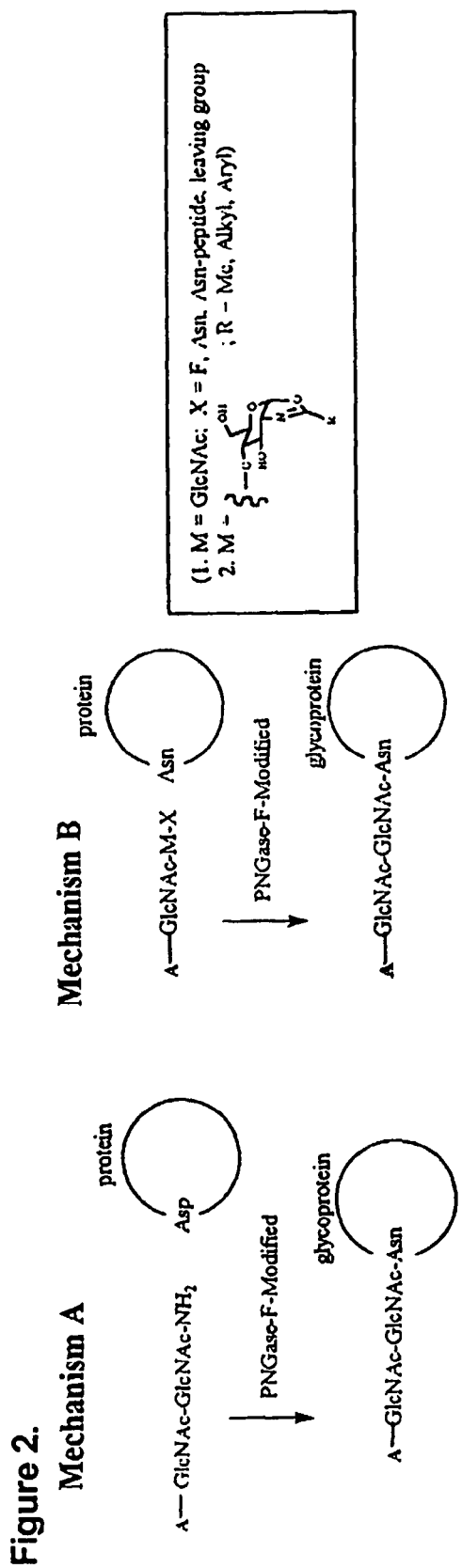
FIG. 2 shows alternate catalytic pathways for methods of the invention.

There are many ways known to those skilled in the art to mutate a peptide-$N^4$-$\beta$-N-acetylglucosamine asparagine peptidase F (PNGaseF), PNGaseAt, PNGaseA, or glycosylasparaginase to generate an enzyme capable of catalyzing the reaction shown in FIG. 2. For example, a *Flavobacterium meningosepticum* PNGaseF gene is synthesized and codon optimized for expression in *E. coli*. In addition, this synthetic gene is designed to preserve the peptide sequence but also to introduce convenient and unique restriction endonuclease sites on either side of the catalytic site residues (Asp60, Glu206 and Glu118). In addition unique restriction sites would be engineered around the important amino acid residues Trp120, Arg248 and His193. PCR primers that introduce Ser, Gly, Ala, Gln or Asn at one or more of these amino acids are designed that also encode the unique restriction endonuclease sites on the 5' and 3' sides of these amino acid residues. The PCR product containing the mutated amino acid (s) is then subcloned into an appropriate inducible expression vector that allows expression of the mutated PNGaseF gene in *E. coli*. The mutated PNGaseF is then assayed for its ability to catalyze the reaction shown in FIG. 2.

The site for mutation in the particular enzyme can be identified using standard techniques. For example, the site can be identified after trapping of the glycosyl-enzyme intermediate in the active site. The intermediate may be trapped, for example, by rapid denaturation of the enzyme after contact with the substrate. Alternatively, the intermediate may be trapped using a modified substrate which forms a relatively stable glycosyl-enzyme intermediate. Once this intermediate has been trapped, the labeled enzyme is then cleaved into peptides by use of a protease or by specific chemical degradation, and the peptide bearing the sugar label then located in a chromatogram or other separation method and its amino acid sequence determined. Comparison of this sequence with that of the intact enzyme readily identifies the amino acid of interest.

The catalytic residues may also be identified in the three-dimensional structure of the enzyme determined by X-ray crystallography or NMR spectroscopy by inspection of the active site region, searching for likely active site residues, e.g., a Glu or Asp residue. For example, using analysis of the crystal structure and site directed mutagenesis of PNGase F, the active site has been characterized, including the sugar binding and catalytic sites (see, Norris et al. *Structure* 2:1049 (1994) and Kuhn et al. *J. Biol. Chem.* 270:29493-29497 (1995)).

In addition to modification of the catalytic residues, alterations of the sugar binding site can also be made to change the specificity of the enzyme for the oligosaccharides portion of the substrate. Point mutations or protein reengineering can be used to change this enzymes sugar specificity, according to standard techniques.

Once the active site residues are identified in one enzyme, the homologous residues in related enzymes can also be found using standard sequence comparison programs. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Mutant genes are typically prepared using site directed mutagenesis to arrive at the desired result. Methods for introducing mutations into polynucleotide sequences are well known. Such well-known methods include site-directed mutagenesis, PCR amplification using degenerate oligonucleotides, and other well-known techniques. See, e.g., Giliman and Smith (1979) *Gene* 8:81-97, Roberts et al. (1987) *Nature* 328: 731-734.

Mutant enzymes according to the invention may be purified from the growth medium of the host organism by column chromatography, for example on DEAE-cellulose if desired. High levels of purity are not required for use in catalyzing oligosaccharide synthesis, however, provided that impurities with wild-type glycosidase activity must be substantially absent.

The mutant enzymes of the invention are used to couple modified glycosyl donors with glycoside acceptors. Any desired carbohydrate structure can be added to a peptide using the methods of the invention. Typically, the structure will be a monosaccharide, but the present invention is not limited to the use of modified monosaccharide sugars; oligosaccharides and polysaccharides are useful as well.

In other embodiments, the glycosyl donor is an activated sugar. Activated sugars, which are useful in the present invention are typically glycosides which have been synthetically altered to include an leaving group. As used herein, the term "leaving group" refers to those moieties, which are easily displaced in enzyme-regulated nucleophilic substitution reactions. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

The donor molecules can be prepared according to standard techniques. For example, glycosyl fluorides can be prepared as generally described in U.S. Pat. No. 5,716,812 or through an imidate intermediate as described by Dullenkopf et al. *Carbohydr Res* 296:135-47 (1996). Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

Preferred donor molecules are halogenated compounds such as glycosyl fluorides or glycosyl chlorides, although other groups which are reasonably small and which function as relatively good leaving groups can also be used. Examples of other glycosyl donor molecules include glycosyl-Asn, glycosyl-Asn-peptide, glycosyl chlorides, glycosyl acetates, glycosyl propionates, and glycosyl pivaloates, and glycosyl molecules modified with substituted phenols.

An exemplary donor molecule of the invention includes a glycosyl residue of the following formula.

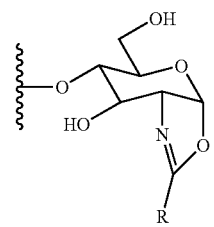

(1)

In Formula 1, the symbol R represents substituted or unsubstituted alkyl or aryl.

The particular saccharides coupled to the protein are not a critical aspect of the invention. Typically, the oligosaccharides will include any bi-, tri- and tetra-antennary structures of N-linked structures. High mannose and hybrid structures can also be transferred including those containing mannose-6-phophate. FIG. 1 provides a summary of exemplary structures that can used in the invention.

In addition to the mutant amidase, the oligosaccharide structures on a peptide can be modified using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycopeptide of the invention. The enzymes are used to alter a saccharide structure on the peptide at any point either before or after the addition of the modified sugar to the peptide.

In another preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 45° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. On an industrial scale, it may be advantageous to immobilize the amidase on a solid support to facilitate its removal from a batch of product and subsequent reuse. Such immobilization can be accomplished by use of a fusion protein in which the mutant glycoside is engineered onto another protein with high affinity for an insoluble matrix. Techniques for immobilizing proteins on solid supports are well known in the art. For example, a fusion protein with a cellulose binding protein prepared in the manner described by Ong et al., *Biotechnology* 7:604-607 (1989) could be used in accordance with the invention.

In other embodiments, the target glycopeptide is immobilized on a solid support. Preferably, the target glycopeptide is reversibly immobilized so that the glycopeptide can be released after the glycosylation reaction is completed. The term "solid support" also encompasses semi-solid supports. Many suitable matrices are known to those of skill in the art. Ion exchange, for example, can be employed to temporarily immobilize a glycopeptide on an appropriate resin while the glycosylation reaction proceeds. A ligand that specifically binds to the glycopeptide of interest can also be used for affinity-based immobilization. Antibodies that bind to a glycopeptide of interest are suitable; where the glycopeptide of interest is itself an antibody or fragment thereof, one can use protein A or G as the affinity resin. Dyes and other molecules that specifically bind to a protein of interest that is to be glycosylated are also suitable.

In the discussion that follows, methods of use in conjunction with the invention are exemplified by the conjugation of sialic acid moiety to a peptide, which is glycosylated by a method of the invention. The focus of the following discussion on the use of sialic acid and glycosylated peptides is for clarity of illustration and is not intended to imply that the invention is limited to the conjugation of these two partners. One of skill understands that the discussion is generally applicable to the additions of glycosyl moieties other than sialic acid.

In general, an acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the acceptor is assembled by attaching a galactose residue to, for example, a GlcNAc or another appropriate saccharide moiety that is linked to the peptide. The method includes incubating the peptide to be modified with a reaction mixture that contains a suitable amount of a galactosyltransferase (e.g., galβ1,3 or galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

The examples set forth above provide an illustration of the power of the methods set forth herein. Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, an existing sialic acid is removed from a glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid.

One can assess differences in glycosylation pattern not only by structural analysis, but also by comparison of one or more biological activities of the protein. The glycopeptide produced by the methods of the invention typically exhibit an improvement in one more biological activities as compared to the unmodified glycopeptide. For example, glycopeptides of the invention can have greater therapeutic efficacy as measured by solubility, resistance to proteolytic attack and thermal inactivation, immunogenicity, half-life, bioactivity, stability and the like. The amount of the improvement observed is preferably statistically significant, and is more preferably at least about a 50% improvement, and still more preferably is at least about 80%.

i. Enzymes

1. Glycosyltransferases

Glycosyltransferases catalyze the addition of activated sugars (e.g., donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize a selected glycosyl donor moiety as a sugar donor. Examples of such enzymes include Leloir pathway glycosyltransferase, such as gal actosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., Taniguchi et al., 2002, Handbook of glycosyltransferases and related genes, Springer, Tokyo; and "The WWW Guide To Cloned Glycosyltransferases," (available at www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galactunoric acid transferases, and oligosaccharyltransferases. Suitable glycosyltransferases include those obtained from eukaryotes, as well as from prokaryotes.

A number of methods of using glycosyltransferases to synthesize desired oligosaccharide structures are known and are generally applicable to the instant invention. Exemplary methods are described, for instance, WO 96/32491, Ito et al., Pure Appl. Chem. 65: 753 (1993), and U.S. Pat. Nos. 5,352,670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

DNA which encodes the enzyme glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotides probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotides primers being produced from the glycosyltransferases gene sequence. See, U.S. Pat. No. 4,683,195 to Mullis et al. and U.S. Pat. No. 4,683,202 to Mullis.

The glycosyltransferases enzyme may be synthesized in host cells transformed with vectors containing DNA encoding the glycosyltransferases enzyme. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transform ants.

a) Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190: 1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-α-fucosyltransferases (FTIV, FTV, FTVI) which are found in human serum. FTVII (E.C. No. 2.4.1.65), a sialyl α(2→3) Galβ(1→3) GlcNAcβ fucosyltransferase, has also been characterized. A recombinant form of the Galβ(1→3,4) GlcNAcβ-α(1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

b) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)).

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe,* Chapell et al., *Mol Biol. Cell* 5: 519-528 (1994)).

The production of proteins such as the enzyme GalNAc $T_{1-XX}$ from cloned genes by genetic engineering is well known. See, e.g., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

c) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 2).

TABLE 2

Sialyltransferases which use the Galβ1,4GlcNAc sequence as an acceptor substrate.

| Sialyltransferase | Source | Sequence(s) formed | Ref. |
|---|---|---|---|
| ST6Gal I | Mammalian | NeuAcI2,6Galβ1,4GlCNAc- | 1 |
| ST3Gal III | Mammalian | NeuAcI2,3Galβ1,4GlCNAc-<br>NeuAcI2,3Galβ1,3GlGNAc- | 1 |
| ST3Gal IV | Mammalian | NeuAcI2,3Galβ1,4GlCNAc-<br>NeuAcI2,3Galβ1,3GlCNAc- | 1 |
| ST6Gal II | Mammalian | NeuAcI2,6Galβ1,4GlCNA | ** |
| ST6Gal II | photobacterium | NeuAcI2,6Galβ1,4GlCNAc- | 2 |
| ST3Gal V | *N. meningitides N. gonorrhoeae* | NeuAcI2,3Galβ1,4GlCNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1, 3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from Campylobacter jejuni, including the α(2,3). See, e.g, WO99/49051.

Other sialyltransferases, including those listed in Table 4, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

d) Other Glycosyltransferases

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., Proc. Natl. Acad. Sci. USA 91: 5977 (1994)) or Alg5 (Heesen et al., Eur. J. Biochem. 224: 71 (1994)).

N-acetylgalactosaminyltransferases are also of use in practicing the present invention. Suitable N-acetylgalactosaminyltransferases include, but are not limited to, α(1,3) N-acetylgalactosaminyltransferase, β(1,4) N-acetylgalactosaminyltransferases (Nagata et al., J. Biol. Chem. 267: 12082-12089 (1992) and Smith et al., J. Biol. Chem. 269: 15162 (1994)) and polypeptide N-acetylgalactosaminyltransferase (Homa et al., J. Biol. Chem. 268: 12609 (1993)). Suitable N-acetylglucosaminyltransferases include GnTI (2.4.1.101, Hull et al., BBRC 176: 608 (1991)), GnTII, GnTIII (Ihara et al., J. Biochem. 113: 692 (1993)), GnTIV, and GnTV (Shoreiban et al., J. Biol. Chem. 268: 15381 (1993)), O-linked N-acetylglucosaminyltransferase (Bierhuizen et al., Proc. Natl. Acad. Sci. USA 89: 9326 (1992)), N-acetylglucosamine-1-phosphate transferase (Rajput et al., Biochem J. 285: 985 (1992), and hyaluronan synthase.

Mannosyltransferases are of use to transfer modified mannose moieties. Suitable mannosyltransferases include α(1,2) mannosyltransferase, α(1,3) mannosyltransferase, α(1,6) mannosyltransferase, α(1,4) mannosyltransferase, Dol-P-Man synthase, OCh1, and Pmt1 (see, Kornfeld et al., Annu. Rev. Biochem. 54: 631-664 (1985)).

Xylosyltransferases are also useful in the present invention. See, for example, Rodgers, et al., Biochem. J., 288: 817-822 (1992); and Elbain, et al., U.S. Pat. No., 6,168,937.

Other suitable glycosyltransferase cycles are described in Ichikawa et al., JACS 114: 9283 (1992), Wong et al., J. Org. Chem. 57: 4343 (1992), and Ichikawa et al. in CARBOHYDRATES AND CARBOHYDRATE POLYMERS. Yaltami, ed. (ATL Press, 1993).

Prokaryotic glycosyltransferases are also useful in practicing the invention. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions (Preston et al., Critical Reviews in Microbiology 23(3): 139-180 (1996)). Such enzymes include, but are not limited to, the proteins of the rfa operons of species such as E. coli and Salmonella typhimurium, which include a β1,6 galactosyltransferase and a β1,3 galactosyltransferase (see, e.g., EMBL Accession Nos. M80599 and M86935 (E. coli); EMBL Accession No. S56361 (S. typhimurium)), a glucosyltransferase (Swiss-Prot Accession No. P25740 (E. coli), an β1,2-glucosyltransferase (rfaJ) (Swiss-Prot Accession No. P27129 (E. coli) and Swiss-Prot Accession No. P19817 (S. typhimurium)), and an β1,2-N-acetylglucosaminyltransferase (rfaK) (EMBL Accession No. U00039 (E. coli). Other glycosyltransferases for which amino acid sequences are known include those that are encoded by operons such as rfaB, which have been characterized in organisms such as Klebsiella pneumoniae, E. coli, Salmonella typhimurium, Salmonella enterica, Yersinia enterocolitica, Mycobacterium leprosum, and the rh1 operon of Pseudomonas aeruginosa.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P_k$ blood group trisaccharide sequence, D-galactosyl-α-1,4-D-galactosyl-β-1,4-D-glucose, which have been identified in the LOS of the mucosal pathogens Neisseria gonnorhoeae and N. meningitidis (Scholten et al., J. Med. Microbiol. 41: 236-243 (1994)). The genes from N. meningitidis and N. gonorrhoeae that encode the glycosyltransferases involved in the biosynthesis of these structures have been identified from N. meningitidis immunotypes L3 and L1 (Jennings et al., Mol. Microbiol. 18: 729-740 (1995)) and the N. gonorrhoeae mutant F62 (Gotshlich, J. Exp. Med. 180: 2181-2190 (1994)). In N. meningitidis, a locus consisting of three genes, IgtA, IgtB and IgE, encodes the glycosyltransferase enzymes required for addition of the last three of the sugars in the lacto-N-neotetraose chain (Wakarchuk et al., J. Biol. Chem. 271: 19166-73 (1996)). Recently the enzymatic activity of the IgtB and IgtA gene product was demonstrated, providing the first direct evidence for their proposed glycosyltransferase function (Wakarchuk et al., J. Biol. Chem. 271(45): 28271-276 (1996)). In N. gonorrhoeae, there are two additional genes, IgtD which adds .beta.-D-GalNAc to the 3 position of the terminal galactose of the lacto-N-neotetraose structure and IgtC which adds a terminal α-D-Gal to the lactose element of a truncated LOS, thus creating the $P_k$ blood group antigen structure (Gotshlich (1994), supra.). In N. meningitidis, a separate immunotype L1 also expresses the $P_k$ blood group antigen and has been shown to carry an IgtC gene (Jennings et al., (1995), supra.). Neisseria glycosyltransferases and associated genes are also described in U.S. Pat. No. 5,545,553 (Gotschlich). Genes for α1,2-fucosyltransferase and α1,3-fucosyltransferase from Helicobacter pylori has also been characterized (Martin et al., J. Biol. Chem. 272: 21349-21356 (1997)). Also of use in the present invention are the glycosyltransferases of Campylobacter jejuni (see, for example, afmb.cnrs-mrs.fr/~pedro/CAZY/gtf_42.html).

2. Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., J. Biol. Chem. 270: 18575-18580 (1995); GenBank Accession No. D49915), glycosaminoglycan N-acetylglucosamine N-deacetylase/N-sulfotransferase 1 (Dixon et al., Genomics 26: 239-241 (1995); UL18918), and glycosaminoglycan N-acetylglucosamine N-deacetylase/N-sulfotransferase 2

(murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

3. Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for volatilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β-D-galactosyl-1,4-N-acetyl-D-glucosaminide α-1,3-galactosyltransferase was transfected into COS-1 cells. The transfected cells were then cultured and assayed for α1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

4. Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar which is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Protein Remodeling and Purification

The methods presented herein can be practiced in any useful order on peptides and glycopeptides that are in crude form, e.g., as expressed, are partially purified or are fully purified. For example, in one embodiment, a peptide or glycopeptide is expressed, purified, remodeled using a method of the invention and subsequently purified. In another exemplary embodiment, a peptide or glycopeptide is expressed, and isolated in crude form. The crude material is remodeled using a method of the invention and the remodeled peptide or glycopeptide is purified. In yet another exemplary embodiment, the expressed peptide or glycopeptide is partially purified, e.g, to remove cellular debris, remodeled and subsequently purified. Other variations on these schemes will be apparent to those of skill in the art and they are within the scope of the present invention.

Purification of Peptide Conjugates and Oligosaccharides a. Oligosaccharide Purification The reagent oligosaccharides produced by the above processes can be used without purification. However, it is usually preferred to recover the product. Standard, well known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes which pass monovalent salts but retain polyvalent salts and uncharged solutes larger than about 100 to about 4,000 Daltons, depending upon the membrane used. Thus, in a typical application, saccharides prepared by the methods of the present invention will be retained in the membrane and contaminating salts will pass through. Additional purification techniques include recrystallization, chromatography (silica, reversed phase, ion exchange) and precipitation.

b. Protein (Glycoprotein) Purification

If the modified glycopeptide is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycopeptide may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycopeptide.

The modified glycopeptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography, may be utilized to purify the modified glycopeptide. These include methods using antibodies, cofactors, substrates or other small molecule agent that selectively binds to the protein of interest.

Affinity tags on the mutant amidase to allow for the simple removal from the reaction mixture.

The Compositions

In another aspect, the present invention provides compositions of glycopeptides prepared by the method of the invention. Using the methods of the invention, it is possible to substantially completely remodel a particular glycosyl residue on a glycopeptide. Thus, in an exemplary embodiment, the invention provides a glycopeptide in which at least about 80% of a population of a selected acceptor moiety on the glycopeptide is glycosylated with the glycosyl residue added by the mutant amidase.

Numerous reaction formats, e.g., solid phase and solution methodologies, will suggest themselves. In an exemplary embodiment, the method of the invention is used to produce a glycopeptide that is attached to a solid support.

The amino acid sequence of the glycopeptides of the invention can be either full-length or truncated. Exemplary proteins include interferon beta, interferon omega, enbrel, EPO, NESP, FSH and the Blood Factors (VIIa, IX, VIII).

Pharmaceutical Formulations

The compounds produced by the methods of the invention can then be used in a variety of applications, e.g., as antigens, diagnostic reagents, or as therapeutics. Thus, the present invention also provides pharmaceutical compositions which can be used in treating a variety of conditions. The pharmaceutical compositions are comprised of glycopeptides made according to the methods described above.

Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously or subcutaneous. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like. Exemplary buffers include phosphate, histidine, glycine and combinations thereof which can also contain excepients such as sugars (i.e. trehalose, mannose, sucrose, glucose, galactose and sialic acid), salts (i.e. sodium chloride, potassium chloride, magnesium salts, calcium salts), proteins (i.e. albumin), detergents (i.e. polysorbate 80) and preservatives (i.e. sodium benzoate).

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8. In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion which is firmly embedded and anchored in the membrane. It must also have a reactive portion which is chemically available on the aqueous surface of the liposome. The reactive portion is selected so that it will be chemically suitable to form a stable chemical bond with the targeting agent or carbohydrate which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The blood-residency of therapeutic glycopeptides can also be enhanced with polyethylene glycol (PEG). Chemical modification of proteins with PEG (PEGylation) increases their molecular size and steric hindrance, both of which are dependent on the PEG attached to the protein. This results in an improvement of plasma half-lives and in proteolytic-stability, and a decrease in immunogenicity and hepatic uptake (Chaffee et al. *J. Clin. Invest.* 89:1643-1651 (1992); Pyatak et al. *Res. Commun. Chem. Pathol Pharmacol.* 29:113-127 (1980)). PEGylation of interleukin-2 has been reported to increase its antitumor potency in vivo (Katre et al. *Proc. Natl. Acad. Sci. USA.* 84:1487-1491 (1987)) and PEGylation of an F (ab')2 derived from the monoclonal antibody A7 has improved its tumor localization (Kitamura et al. *Biochem. Biophys. Res. Commun.* 28:1387-1394 (1990)).

The compositions containing the glycopeptides can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this use will depend on the severity of the disease and the weight and general state of the patient, but generally range from about 0.5 mg to about 2,000 mg of glycopeptide per day for a 70 kg patient, with dosages of from about 5 mg to about 200 mg of the compounds per day being more commonly used.

In prophylactic applications, compositions containing the glycopeptides of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the glycopeptides of this invention sufficient to effectively treat the patient.

The glycopeptides may also find use as diagnostic reagents. For example, labeled compounds can be used to locate areas of inflammation or tumor metastasis in a patient suspected of having an inflammation. For this use, the compounds can be labeled with appropriate radioisotopes, for example, $^{125}$I, $^{14}$C, or tritium.

The glycopeptides of the invention can be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the glycopeptide of the invention. Antibody-producing cells obtained from the immunized animals are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

The following examples are offered to illustrate, but not to limit the present invention.

EXAMPLE 1

This example describes the modification of PNGase-F for use in the methods of the invention.

PNGase F is a 34.7 kDa amidohydrolase secreted by *Flavobacterium meningosepticum*. The enzyme hydrolyses N-linked oligosaccharide chains of glycopeptides, converting the asparagine to aspartic acid with the release of ammonia and the intact oligosaccharide chain. Enzymatic activity of PNGase F requires recognition of both the peptide and carbohydrate components of the substrate.

The catalytic mechanism for the mutant enzyme can catalyze either of two pathways (FIG. 2). Pathway A facilitates the synthesis of the oligosaccharide-protein bound using the reverse reaction of a peptidase hydrolysis step. The oligosaccharide contains an amino glycoside or a specific or complex mixture of oligosaccharide structures recognized by the enzyme. Pathway B utilizes an activated oligosaccharide and proceeds with addition of the sugar to Asn residues of the protein. The activated sugar can contain F, Asn, Asn-peptide or other leaving group at the reducing termini. The activated sugar could also contain the 1,2-oxazoline of GlcNAc at the reducing sugar.

Mutation of the PNGase-F protein is carried out as described above. The known active site residues include Asp (60), Glu (206), Glu (118), Trp (120), Arg (248) and His (193). One or more of these amino acids is modified to improve the synthetic ability of the enzyme.

In another example, each of the three acidic residues, Asp (60), Glu (206) and Glu (118), are modified, (see Kuhn et al, J. Biol. Chem. 270:9493 (1995)). All three residues are in the active site of the enzyme and in contact directly or indirectly with the bound sugar. An example of a modification is to change each residue to Asn or Ser.

By using modified PNGase-F, N-linked oligosaccharide structures can be added to any protein of interest whether the protein already has oligosaccharide structures or not. The only requirement is for the protein of interest to contain a peptide sequence recognized by the improved PNGase-F to allow oligosaccharide transfer. Because one can control which oligosaccharide structure is used during protein remodeling as well as the purity of the protein to be remodeled, a new glycopeptide product can be produced with a well defined and quantifiable structure.

EXAMPLE 2

2.1 Introduction of a Bi-Antennary-N-Linked Glycan onto Interferon Beta

A solution of the mutated PNGase F (40,000 Units) is added to a solution of E. coli produced interferon beta (0.35 mmol) dissolved in 100 mL of phosphate buffer (250 mM) at pH 7.5, 0.2% polysorbate 80 and biantennary-glycan (see FIG. 2). The solution is mixed at room temperature. To monitor the reaction, a small aliquot of the reaction is diluted with the appropriate buffer and an IEF gel performed. When the reaction is complete, the reaction mixture is applied to a HIC column (C-4) and a gradient elution performed using a mixture of water and acetonitrile with a low percentage of TFA. Appropriate fractions are combined, polysorbate 80 is added and the pH is adjusted to 7.4. The buffer is exchanged and the solution is concentrated by diafiltration using a 10 K membrane and exchanging against PBS buffer containing polysorbate 80. The product of the reaction is analyzed using SDS PAGE and IEF analysis according to the procedures and reagents supplied by Invitrogen. Samples of native and glycopeptide are dialyzed against water and analyzed by MALDI-TOF MS.

2.2 Introduction of Tetra-Antennary-N-Linked-Glycans onto Erythropoietin

A solution of the mutated N-glycosidase A (1,000,000 Units) is added to a solution of E. coli produced erythropoietin (0.35 mmol) dissolved in 1 L of phosphate/citrate buffer (250 mM) at pH 6.5, 0.02% polysorbate 80 and tetra-antennary-glycan (see FIG. 2). The solution is mixed at room temperature. To monitor the reaction, a small aliquot of the reaction is diluted with the appropriate buffer and a IEF gel performed. When the reaction is complete, the reaction mixture is applied to a HIC column (C-4) and a gradient elution performed using a mixture of water and acetonitrile with a low percentage of TFA. Appropriate fractions are combined, polysorbate 80 is added and the pH adjusted to 7.4. The buffer is exchanged and the solution concentrated by diafiltration using a 10 K membrane and exchanging against PBS buffer containing polysorbate 80. The product of the reaction is analyzed using SDS PAGE and IEF analysis according to the procedures and reagents supplied by Invitrogen. Samples of native and glycopeptide are dialyzed against water and analyzed by MALDI-TOF MS.

2.3 Preparation of Bi-Antennary-Glycan-F (FIG. 2B.1)

The biantennary-N-linked glycan isolated from egg protein (0.5 g) is added to a solution containing pyridine (20 mL) and DMAP (0.1 g). The solution is cooled to 0° C., and acetic anhydride (400 mole eq) is slowly added. The reaction is warmed to 40° C. until the reaction is completed as determined by TLC. The reaction mixture is concentrated to dryness and ethyl acetate is added to dissolve the residue. The organic layer is washed with water, sat. sodium bicarbonate/water, water and was then dried ($Na_2SO_4$). After filtration, the filtrate is concentrated to dryness and chromatography (silica) performed on the residue. Appropriate fractions were collected, concentrated and characterized by NMR and MS.

The solid is dissolved in pyridine and cooled to 0° C. A solution of pyridine-HF complex was then added to the solution, which is stirred for 8 hrs after the addition is complete. The reaction mixture is then slowly added to a sat. sodium bicarbonate solution at 0° C. and the pH of the aqueous layer maintained above 7.0. When addition is complete, the aqueous solution is extracted with ethyl acetate (2×), and the organic layer is washed with water and dried. Concentration affords a solid which is immediately dissolved in methanol, and sodium methoxide in methanol is added until the pH of the solution is above 14. The reaction mixture is stirred at 40° C. while maintaining the pH of the reaction mixture above pH 12. When the reaction is complete, the solution is neutralized with acetic acid and the solution concentrated to dryness. Chromatography (silica) is performed on the residue and the appropriate fractions are collected, combined and concentrated. The structure of the product is verified by NMR and MS.

2.4 Preparation of Tetra-Antennary-Glycan-Oxazaline (FIG. 2B.2)

The synthesized tetra-antennary-N-linked glycan (0.5 g) is added to a solution containing pyridine (20 mL) and DMAP (0.1 g). The solution is cooled to 0° C., and acetic anhydride (400 mole eq) is slowly added. The reaction is warmed to 40° C. until the reaction is complete as determined by TLC. The reaction mixture is concentrated to dryness and ethyl acetate is added to dissolve the residue. The organic layer is washed with water, sat. sodium bicarbonate/water, water and is then dried ($Na_2SO_4$). After filtration, the filtrate is concentrated to dryness and chromatography (silica) performed on the residue. Appropriate fractions are collected, concentrated and characterized by NMR and MS.

The resulting solid is dissolved in dichloromethane and $BF_3$ added and the reaction mixture is stirred at room temperature. When the reaction is complete by TLC, the reaction mixture is washed with water/sodium bicarbonate and dried. The mixture is then filtered and the filtrate is concentrated.

The residue is then dissolved in methanol, and sodium methoxide in methanol is added until the pH of the solution is above 14. The reaction mixture is stirred at 40° C., while maintaining the pH of the reaction mixture above pH 12. When the reaction is complete, the solution is neutralized with acetic acid and concentrated to dryness. Chromatography (silica) is then performed on the residue and appropriate fractions are collected. These are combined, concentrated and the structure verified by NMR and MS.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An in vitro method of glycosylating a polypeptide comprising an Asn or an Asp residue, the method comprising the steps of contacting the polypeptide with a glycosyl donor molecule having a GlcNAc residue and a PNGase-F amidase under conditions suitable for the linkage of the GlcNAc residue on the glycosyl donor molecule to the Asn or Asp residue on the polypeptide,
   wherein said PNGase-F amidase comprises at least one amino acid substitution of an amino acid residue for an active site acidic amino acid residue selected from the group consisting of Asp at position 60, Glu at position 206 and Glu at position 118 corresponding to a wild-type PNGase-F amidase sequence (SEQ ID NO:01).

2. The method of claim 1, wherein the glycosyl donor molecule is modified with a leaving group at the reducing terminus of the molecule.

3. The method of claim 2, wherein the leaving group is a halogen.

4. The method of claim 3, wherein the halogen is fluoride.

5. The method of claim 2, wherein the leaving group is a Asn, or a Asn-peptide moiety.

6. The method of claim 1, wherein the GlcNAc residue on the glycosyl donor molecule is modified.

7. The method of claim 6, wherein the GlcNAc residue comprises a 1,2 oxazoline moiety.

8. The method of claim 1, wherein the glycosyl donor molecule comprises a bi, tri, or tetra-antennary structure.

9. The method according to claim 1, wherein the glycosyl donor comprises a linkage between GlcNAc and mannose.

10. The method according to claim 1, wherein the glycosyl donor comprises a high mannose N-linked structure.

11. The method according to claim 1, wherein the glycosyl donor comprises mannose-6-phosphate.

12. The method of claim 1, wherein the PNGase-F amidase is attached to a solid support.

13. The method of claim 1, wherein the glycopeptide is reversibly attached to a solid support.

14. The method of claim 1, further comprising the step of recombinantly expressing the polypeptide in a prokaryotic cell.

15. The method of claim 13, wherein the prokaryotic cell is a bacterial cell.

16. The method of claim 1, further comprising the step of recombinantly expressing the polypeptide in an eukaryotic cell.

17. The method of claim 16, wherein the eukaryotic cell is a yeast cell or an insect cell.

18. The method of claim 16, further comprising the step of contacting the polypeptide with a wild type amidase to cleave carbohydrate structures from the polypeptide before the step of contacting the polypeptide with the PNGase-F amidase.

19. The method according to claim 1, wherein the polypeptide comprises an acceptor moiety for a glycosyltransferase, and the method further comprises contacting the polypeptide with a reaction mixture that comprises a glycosyl donor moiety and a glycosyltransferase under conditions appropriate to transfer a glycosyl residue from the glycosyl donor moiety to the glycosyltransferase acceptor moiety.

20. A composition comprising a glycopeptide glycosylated according to the method of claim 1.

21. The composition of claim 20, wherein at least 80% of the acceptor moieties on the glycopeptide are glycosylated.

22. The composition of claim 20, wherein glycopeptide is attached to a solid support.

23. The composition of claim 20, wherein the glycopeptide is a full-length glycopeptide.

24. The composition according to claim 20, wherein the glycopeptide is on a cell.

25. A large-scale in vitro method for modifying the glycosylation pattern of a polypeptide comprising an acceptor moiety for a PNGase-F amidase, the method comprising:
   contacting at least about 500 mg of the polypeptide with a reaction mixture that comprises a glycosyl donor moiety for the PNGase-F amidase under conditions appropriate to transfer a glycosyl residue from the glycosyl donor moiety to the acceptor moiety, thereby producing the glycopeptide having modified glycosylation patterns,
   wherein said PNGase-F amidase comprises at least one amino acid substitution of an amino acid residue for an active site acidic amino acid residue selected from the group consisting of Asp at position 60, Glu at position 206 and Glu at position 118 corresponding to a wild-type PNGase-F amidase sequence (SEQ ID NO:01).

26. The method according to claim 25, wherein the modified glycosylation pattern is a substantially uniform glycosylation pattern.

27. The method according to claim 25, wherein the polypeptide is a recombinant polypeptide.

28. The method according to claim 25, wherein the polypeptide comprises an acceptor moiety for a glycosyltransferase, and the method further comprises contacting the polypeptide with a reaction mixture that comprises a glycosyl donor moiety and a glycosyltransferase under conditions appropriate to transfer a glycosyl residue from the glycosyl donor moiety to the glycosyltransferase acceptor moiety.

29. A peptide prepared by a method according to claim 25.

30. A large-scale in vitro method of producing a glycopeptide, the method comprising:
   (a) contacting at least about 500 mg of a polypeptide with a reaction mixture that comprises a glycosyl donor moiety and a PNGase-F amidase under conditions appropriate to transfer a glycosyl residue from the glycosyl donor moiety to a glycosyl acceptor moiety on the polypeptide; and
   (b) terminating the transfer of the glycosyl residue to the glycosyl acceptor when the glycosylation pattern is substantially identical to the known glycosylation pattern is obtained,
   wherein said PNGase-F amidase comprises at least one amino acid substitution of an amino acid residue for an active site acidic amino acid residue selected from the group consisting of Asp at position 60, Glu at position 206 and Glu at position 118 corresponding to a wild-type PNGase-F amidase sequence (SEQ ID NO:01).

31. The method according to claim 30, wherein the terminating is due to exhausting in the reaction mixture a member selected from the PNGase-F amidase, the glycosyl donor, the glycosyl acceptor, quench with a chelator and combinations thereof.

32. The method according to claim 30, wherein the polypeptide is a recombinant polypeptide.

33. A peptide prepared by a method according to claim 30.

* * * * *